United States Patent [19]

Nastari et al.

[11] Patent Number: 4,643,178

[45] Date of Patent: Feb. 17, 1987

[54] SURGICAL WIRE AND METHOD FOR THE USE THEREOF

[75] Inventors: John J. Nastari, N. Providence; Walter C. Cotter, Providence, both of R.I.

[73] Assignee: Fabco Medical Products, Inc., Lincoln, R.I.

[21] Appl. No.: 603,228

[22] Filed: Apr. 23, 1984

[51] Int. Cl.$^4$ ............................................. A61F 5/04
[52] U.S. Cl. .......................... 128/92 YD; 128/92 VK
[58] Field of Search .............. 128/92 R, 92 B, 335.5, 128/326, 69, 92 G

[56] References Cited

U.S. PATENT DOCUMENTS

| | | | |
|---|---|---|---|
| 505,148 | 9/1893 | Weaver | 128/335.5 |
| 887,074 | 5/1908 | Depage | 128/92 B |
| 2,012,776 | 8/1935 | Roeder | 128/326 |
| 2,093,145 | 9/1937 | Carruthers | 128/92 R |
| 2,591,063 | 4/1952 | Goldberg | 128/335.5 |
| 3,130,728 | 4/1964 | Pearson et al. | 128/335.5 |
| 3,311,110 | 3/1967 | Singerman et al. | 128/335.5 |
| 4,557,259 | 12/1985 | Wu | 128/92 E |
| 4,570,618 | 2/1986 | Wu | 128/92 E |

Primary Examiner—Gene Mancene
Assistant Examiner—C. W. Shedd
Attorney, Agent, or Firm—Salter & Michaelson

[57] ABSTRACT

A surgical wire and a method for the use thereof for interconnecting adjacent portions of bone structures are disclosed. The wire is preferably made of a flexible and malleable corrosion-resistant metal, such as a surgical grade of stainless steel, and it includes a main portion, a tapered portion which extends from the main portion, and a leader portion which extends from the tapered portion and has a substantially reduced diameter with respect to the main portion. The method is carried out by first threading the leader portion around a portion of a bone structure and then further advancing the leader portion to thread the main portion of the wire around the bone structure portion. The main portion of the wire is then secured to an adjacent portion of a bone structure to provide support for one of the two bone structure portions. The method has particular application in spinal surgery for interconnecting adjacent vertebrae to promote fusion of a fractured vertebra. In spinal fusion applications of the method, the leader portion is preferably connected to a curved surgical needle, and the needle is used for threading the leader portion through the spinal foramen of a vertebra along the underside of the lamina thereof so that damage to the spinal cord is avoided.

2 Claims, 8 Drawing Figures

U.S. Patent   Feb. 17, 1987   Sheet 1 of 2   4,643,178
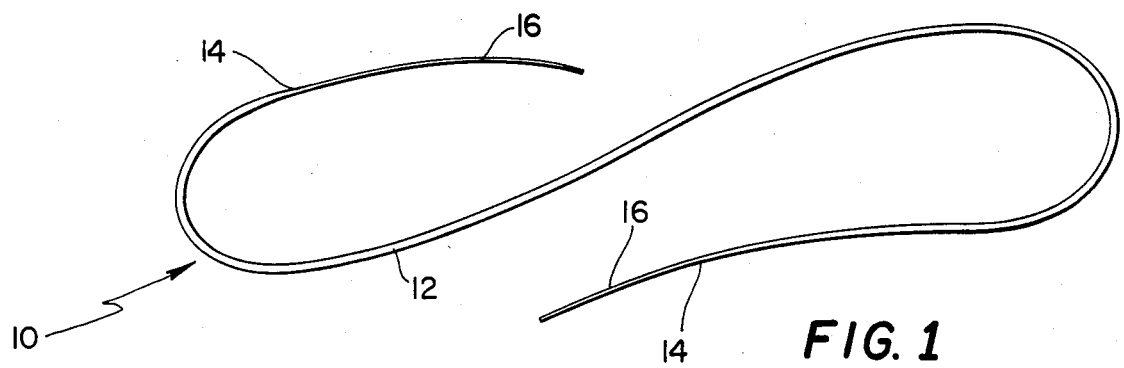
FIG. 1
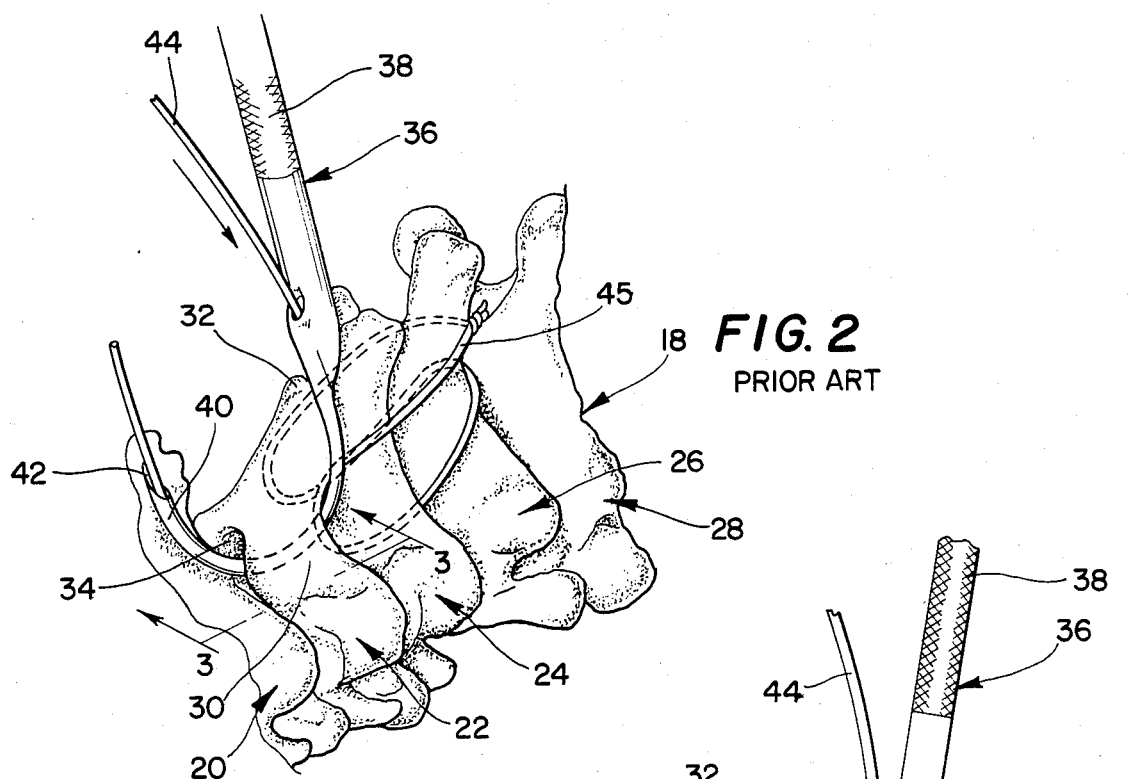
FIG. 2 PRIOR ART
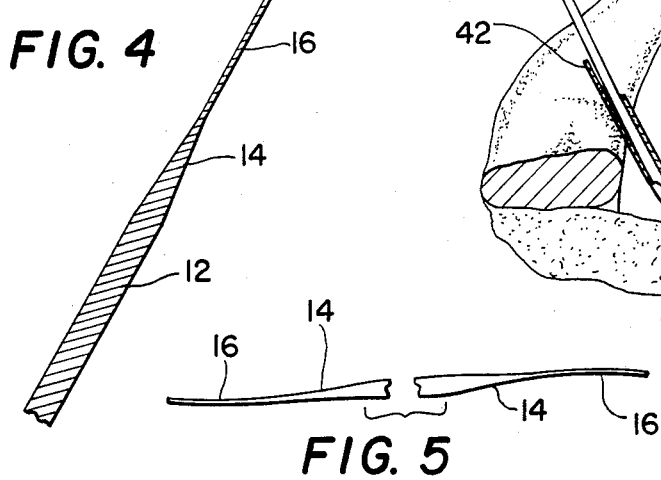
FIG. 4
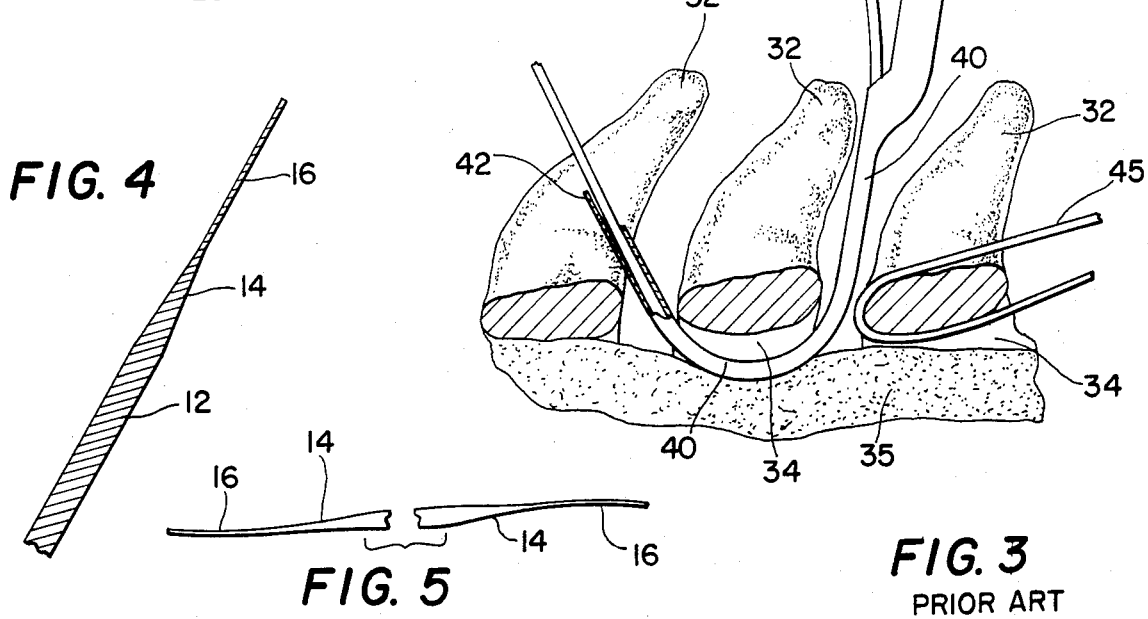
FIG. 5
FIG. 3 PRIOR ART

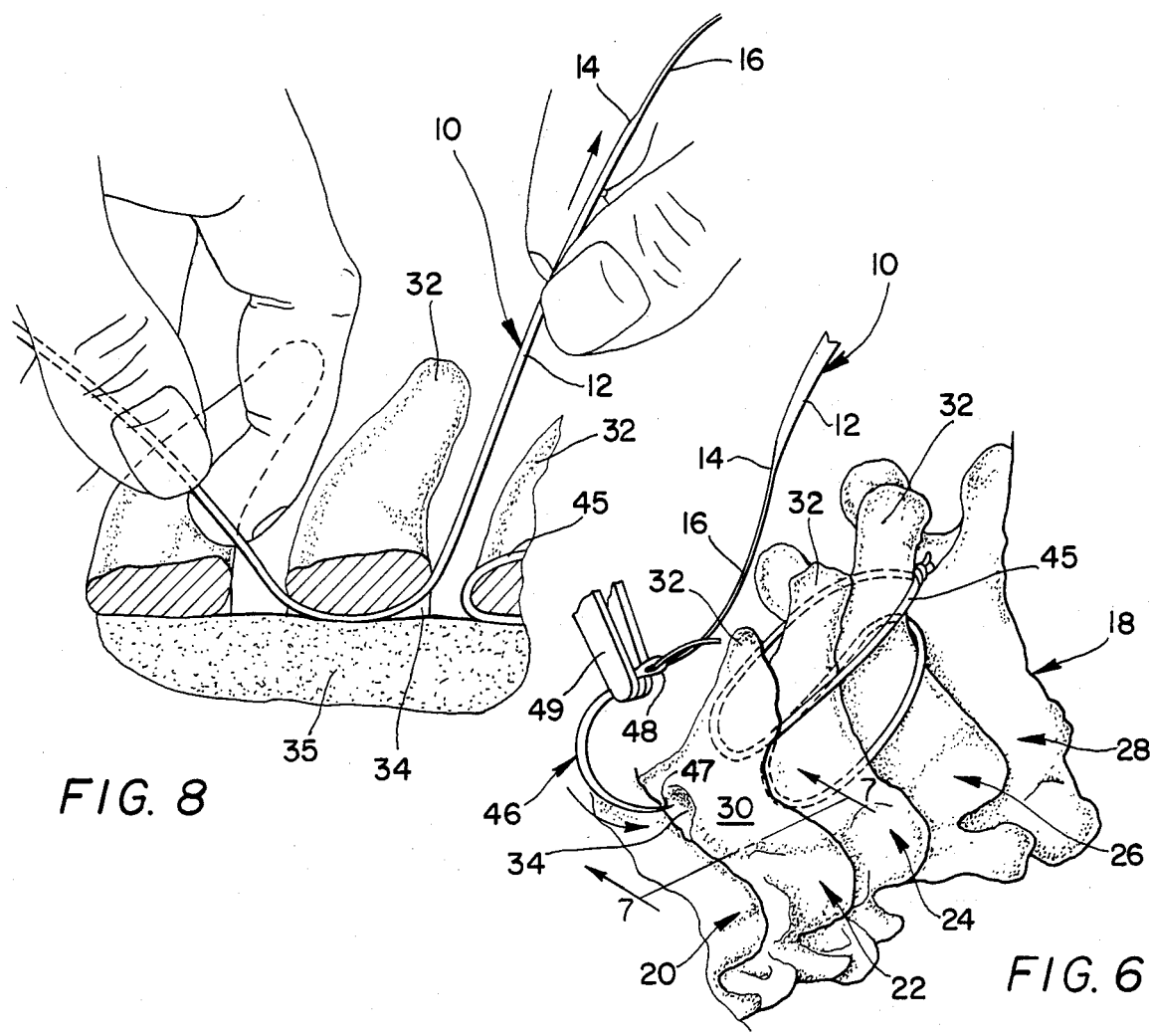
FIG. 8
FIG. 6
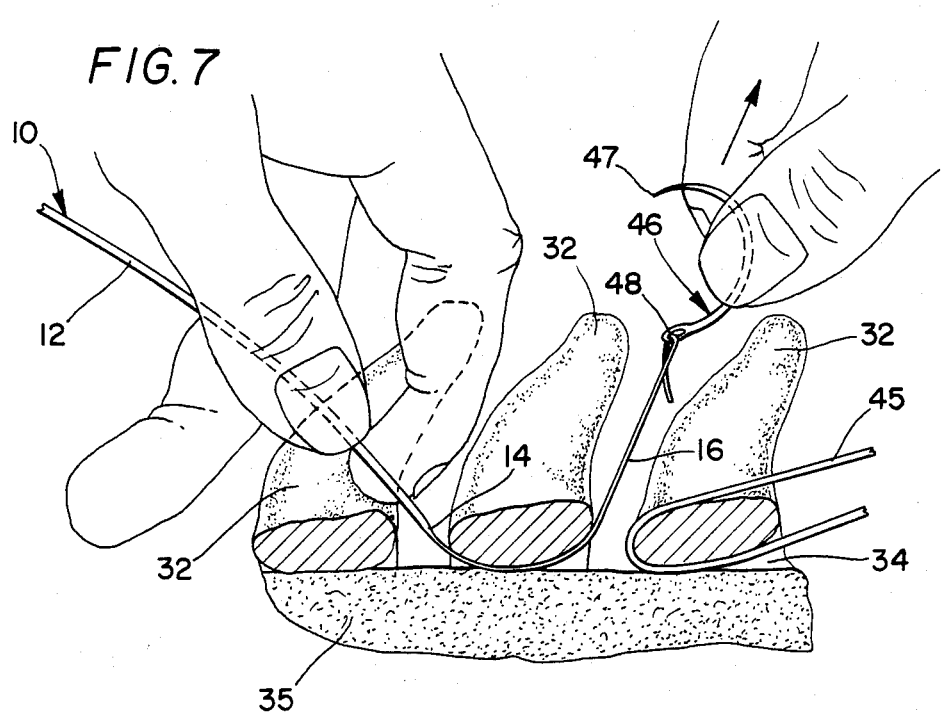
FIG. 7

SURGICAL WIRE AND METHOD FOR THE USE THEREOF

BACKGROUND AND SUMMARY OF THE INVENITION

The instant invention relates to surgical equipment and procedures and more particularly to a novel surgical wire and to a method for the use thereof for interconnecting two or more adjacent bone structures and/or adjacent portions of fractured bone structures.

A significant factor in the healing process for any bone fracture is the degree to which the fractured portions of bone can be maintained in properly set orientations during the healing process. The problems of properly setting and securing fractured portions of bone structures are solved relatively easily in cases of relatively minor bone fractures where the fractured bone portions can be set without surgery and thereafter maintained in proper orientations with external splints or casts. However, in cases where more serious or complicated fractures are involved, surgery is often required to properly set the fractured portions of bone, and various types of hardware, such as screws, pins, and wires, are frequently required in order to secure the fractured bone portions in properly set orientations. Although many of the surgical procedures which are utilized for setting bone structures have become relatively routine, there is always a risk that surgery will result in inadvertent damage to nerves, tendons, or other portions of the anatomy.

Fractures of the vertebrae in the spinal column are often very serious fractures, particularly because they frequently involve damage to the spinal cord which can result in varying degrees of paralysis. Further, surgery is often required to set and/or immobilize fractured vertebrae in order to assure proper fusion of the fractured portions of bone, and even the most delicate heretoforeknown surgical procedures have, on occasion, resulted in inadvertent damage to the spinal cords of patients. One frequently used procedure for setting a fractured vertebra in the spinal column, particularly in the cervical area of the spinal column, is to wire the fractured vertebra to one or more adjacent vertebrae in order to provide support for the fractured vertebra to assure that it is retained in a desired orientation during the healing process. The procedure which has heretofore been followed for installing wires in the spinal column is an extremely delicate one, which requires the passing of one or more surgical wires beneath the laminae of one or more vertebrae so that the wire or wires actually pass through the spinal foramen of the vertebrae adjacent the spinal cord. While a properly installed wire which is positioned so that it is adjacent the wall of the foramen beneath the lamina can be accommodated in the spinal foramen of a vertebra for an indefinite period of time without causing substantial trauma to a patient, the heretofore-known procedures for installing such wires have been extremely delicate procedures, and they have, on occasion, resulted in irreparable damage to the spinal cords of patients.

The heretofore-known surgical procedures for passing surgical wires beneath the laminae of vertebrae have generally been carried out by using a surgical instrument comprising an elongated handle portion to which a curved tubular end portion is secured, the end portion having an open tubular terminal end. In order to install a wire in the spinal column of a patient, the wire is inserted into the curved tubular end portion of the instrument, and the end portion is then inserted into the spinal foramen beneath the lamina of a vertebra. Thereafter, further portions of the wire are passed through the curved end portion of the wire passing instrument until the end of the wire can be grasped with a plier or similar grasping instrument, and then the instrument is backed out or withdrawn from the spinal foramen leaving the wire in position beneath the lamina. Once the wire has been passed through the spinal foramen in this manner, it can then be urged into contact with the surface of the lamina so that it does not press against the spinal cord, and the wire can be secured to a portion of an adjaent vertebra in order to provide support or fixation for the fractured vertebrae.

While the heretofore used surgical procedures for installing surgical wires between vertebrae have been successful in a majority of the cases in which they have been applied, they are extremely delicate procedures, and a number of instances have occurred wherein these procedures have resulted in substantial permanent damage to the spinal cords of patients, and in some cases patients have suffered substantial paralysis. Sometimes damage of this type has occurred during the insertion and removal of the curved tubular end portions of instruments through the spinal foramen of the vertebrae of patients. This is particularly true because of the fact that in order to accommodate a surgical wire in the tubular end portion of an instrument of this type, the overall configuration and the sectional dimension of the curved tubular end portion of the instrument must be relatively large, considering that the end portion must actually be passed through the foramen of a vertebra. In this regard, the radius of curvature of the end portion must be great enough to permit a wire to be passed therethrough without binding significantly, and the sectional dimension of the end portion must be relatively large for similar reasons. Further, the tubular opening in the terminal end of the tubular end portion provides an area for tissue, etc., to catch on the end portion as it is passed through the foramen. In addition, the overall construction of the instrument with an elongated handle which is attached to the end portion makes the instrument difficult to manipulate with the degree of precision required for spinal surgery. All of these structural features of the instruments heretofore used for installing wires in the spinal column have contributed to making the heretofore-known surgical procedures for installing surgical wires extremely delicate and high-risk procedures.

Further, oftentimes the heavy guage wire, because of its thickness, cannot be safely passed under the lamina of the spinal foramen. In such instances a compromise is often effected either by reducing the width of the lamina by removing some of the bone of that lamina, thereby weakening that supporting structure and hence jeopardizing the integrity of the fusion, or by using a smaller gauge of wire to effect the boney stabilization, only to have that wire break in the post operative period before bony fusion has occurred, thus again leading to failure of the operation.

The instant invention effectively overcomes these and other disadvantages of the heretofore-known surgical apparatus and procedures for interconnecting adjacent bone structures with surgical wires and the like. The surgical wire of the instant invention comprises an elongated flexible and malleable main portion, a flexible and malleable tapered portion which integrally extends from an end of the main portion, and a flexible and malleable leader portion which is of substantially reduced diameter with respect to the main portion and extends integrally from the reduced end of the tapered portion. The surgical wire of the instant invention is used in the method of the instant invention by first threading the leader portion around a bone structure, preferably by using a surgical needle attached to the leader portion, and then advancing the leader portion so that the main portion of the wire extends around the bone structure. Thereafter the method is completed by securing the wire to an adjacent second bone structure to interconnect the two bone structures, whereby one of the two bone structures provides support for the other.

While the use of the surgical wire of the instant invention in a variety of different surgical procedures of this general type is comtemplated, it has been found that the surgical wire of the instant invention has particular application in a surgical procedure for interconnecting adjacent vertebrae of the spinal column, particularly in the cervical area of the spinal column, to promote proper fusion of the portions of a fractured vertebra. The method of the instant invention for interconnecting adjacent vertebrae comprises interconnecting the vertebrae with the surgical wire of the instant invention by first attaching the leader portion of the wire to a curved surgical needle and then passing the needle through the spinal foramen of a vertebra so that it passes in contact with or at least closely adjacent the wall of the spinal foramen beneath the lamina of the vertebra, and then further advancing the leader portion so that the tapered portion and a portion of the main portion of the surgical wire pass through the spinal foramen in contact with or closely adjacent the wall thereof. The method is then completed by securing the opposite end portions of the main portion to an adjacent vertebra to interconnect the two vertebrae. Preferably these steps are carried out in a series of manipulative operations wherein sequential portions of the wire are gradually urged through the spinal foramen of the vertebra while a certain amount of tension is applied to the opposite end portions of the surgical wire in order to maintain the portion of the wire which is located within the foramen in contact with or at least closely adjacent to the wall of the foramen beneath the lamina so that that the wire does not press against the spinal cord. Further, preferably the surgical needle which is used in the method has a sectional dimension which is generally similar to the sectional dimension of the main portion of the surgical wire, and the leader portion of the surgical wire is threaded through an eye in one end of the needle to interconnect it thereto. Accordingly the sectional dimension of the needle is minimized, and the combined sectional dimension of the needle and the leader portion where it is interconnected to the needle is also minimized in order to minimize the sectional dimension of the hardware which is passed through the foramen. Further, the radius of curvature of the needle can be selected to precisely fit the requirements of each application, and since the needle is only connected to the leader portion which is highly flexible as a result of its reduced diameter, the needle can be delicately manipulated with a high degree of freedom and mobility as it is passed through the foramen. It has been found that for these reasons, when adjaent vertebrae are interconnected in accordance with the method of the instant invention, the risks to the patient are substantially reduced as compared to the risks associated with the heretofore-known methods.

Heretofore-known apparatus representing the closest prior art to the surgical wire of the instant invention of which the applicant is aware are disclosed in the U.S. patents to DePage U.S. Pat. No. 887,074; Carruthers U.S. Pat. No. 2,093,145; Pearson et al U.S. Pat. No. 3,130,728; and Kaufman et al U.S. Pat. No. 3,125,095. However, since none of these references teach the specific structural features of the surgical wire of the instant invention, they are believed to be of only general interest. They are also believed to be of only general interest with regard to the method of installing the wire in accordance with the instant invention.

Accordingly, it is a primary object of the instant invention to provide an effective surgical wire for interconnecting adjacent bone structures in surgical procedures.

Another object of the instant invention is to provide an effective method of interconnecting adjacent bone structures in surgical procedures.

Still another object of the instant invention is to provide an effective method of interconnecting adjacent vertebrae in the spinal column without causing damage to the spinal cord.

An even further object of the instant invention is to provide an improved wire for securing and immobilizing a fractured vertebra in order to promote proper fusion of the fractured portions of the vertebra.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is a perspective view of the surgical wire of the instant invention;

FIG. 2 is a perspective view illustrating the method of the prior art for interconnecting adjacent vertebrae in the spinal column;

FIG. 3 is a sectional view taken along line 3—3 in FIG. 2;

FIG. 4 is a fragmentary sectional view of a portion of the wire of the instant invention;

FIG. 5 is a fragmentary plan view illustrating the opposite end portions of the wire;

FIG. 6 is a perspective view illustrating the method of the instant invention;

FIG. 7 is a sectional view taken along line 7—7 in FIG. 6; and

FIG. 8 is another sectional view illustrating the method of the instant invention.

DESCRIPTION OF THE INVENTION

Referring now to the drawings, the surgical wire of the instant invention is illustrated in FIGS. 1 and 4 through 8 and generally indicated at 10. The wire 10 comprises an elongated flexible and malleable main portion 12, a pair of flexible and malleable tapered portions 14 which extend integrally from the opposite ends of the main portion 12, and a pair of leader portions 16 which are of substantially reduced diameter with respect to the main portion 12 and extend integrally from the reduced ends of the tapered portions 14. Preferably, the wire 10 is constructed of a surgical grade of stainless steel, such as 304 or 316 stainless steel, and it is preferably annealed for increased flexibility. The main portion 12 is preferably approximately 18 gauge, whereas the reduced end portion 16 is preferably approximately 26 gauge, although the embodiment of these portions in other sectional dimensions is contemplated. Further, while the wire 10 includes a tapered portion 14 and a leader portion 16 at each end of the main portion 12, other embodiments of the wire 10 which include a tapered portion 14 and a leader portion 16 at only one end of the main portion 12 are also contemplated.

The use of the wire 10 in accordance with the method of the instant invention is illustrated in FIGS. 6 through 8. The method is generally carried out by threading the leader portion 16 around a bone structure, further advancing the leader portion 16 to thread the main portion 12 around the bone structure and thereafter securing the opposite end portions of the main portion 12 to an adjacent bone structure to interconnect the two bone structures. Although the use of the method for interconnecting various types of bone structures is contemplated, the method is particularly adapted for interconnecting adjacent vertebrae of the spinal column to promote fusion of a fractured vertebra, especially in the cervical area of the spinal column, as illustrated in FIGS. 6 through 8 and as will hereinafter be more fully described.

Referring to FIGS. 2 and 3, the most commonly used heretofore-known method for interconnecting adjacent vertebrae in the cervical area of the spinal column for promoting fusion of a fractured vertebra is illustrated. In this regard, a portion of the cervical area of spinal column is illustrated and generally indicated at 18 in FIG. 2 and comprises a plurality of adjacent vertebrae generally indicated at 20, 22, 24, 26 and 28. Each of the vertebrae 20 through 28 has a lamina region 30, a spinous process 32 and a spinal foramen 34, and an open interior passage extends through each of the vertebrae 20, 22, 24, 26 and 28. Generally, it has been found that when a vertebra of the spinal column is fractured, the most effective way of assuring that it remains properly set and immobilized during the fusion process is to wire it to the two adjacent vertebrae in a surgical procedure in order to provide support for the fractured vertebra. Heretofore, procedures of this type have been carried out utilizing an instrument of the type illustrated and generally indicated at 36 comprising an elongated handle portion 38 and curved tubular end portion 40 which extends integrally from the handle portion 38 and terminates in a tapered open tubular end 42. A conventional elongated surgical wire 44 is installed in the spinal column utilizing the instrument 36 by first inserting an end of the wire 44 into the curved tubular end portion 40 of the instrument 36 and then passing the curved end portion 40 through the foramen 34 of an appropriate vertebra. After the end portion 40 has been passed through the foramen 34, the wire 44 is then further advanced through the end portion 40 until it can be grasped with a plier-like instrument, and then the instrument 36 is manipulated so that the end portion 40 is withdrawn from the foramen 34, leaving the wire 44 therein. The wire 44 is then repositioned adjacent the wall of the respective foramen 34 so that it does not press against the spinal cord 35, and the wire 44 is secured to an adjacent vertebra, preferably by interconnecting the opposite end portions of wire 44 so that the wire 44 extends around the spinous process 32 thereof, and the ends of the wire 44 are cut to the desired lengths. As illustrated in FIG. 2, the vertebra 24 is interconnected to the adjacent vertebra 22 and 26 by this manner in order to provide support for the vertebra 24. Specifically, FIG. 2 illustrates the passing of the wire 44 through the foramen 34 of the vertebra 22 in order to interconnect the vertebrae 22 and 24, whereas a previously installed wire 45 is used to interconnect the vertebrae 24 and 26. The wire 45, which is exemplary of the preferred arrangement of a properly installed wire, extends through the foramen 34 of the vertebra 24, along one side of the spinous process 32 of the vertebra 24, around the spinous process 32 of the vertebra 26, along the opposite side of the spinous process 32 of the vertebra 26, again through the foramen 34 of the vertebra 24, and back around the spinous process of the vertebra 26 in a similar manner, and then the opposite ends of the wire 45 are interconnected. Generally, it has been found that wires installed in the spinal column of a patient in this manner can be tolerated for an indefinite period of time, and normally they do not require removal after the healing or fusion process has been completed.

While the above-described procedure has proven to be an effective method for interconnecting adjacent vertebrae of the spinal column in most cases, it has been found to be an extremely high-risk procedure which can easily result in damage to the spinal cord. Specifically, when a wire 44 is installed in the foramen 34 of a vertebra using the instrument 36, the spinal cord 35 can easily be damaged as the end portion 40 of the instrument is inserted into the foramen 34 and thereafter when it is removed therefrom. Basically, this results from several structural features of the instrument 36 which make it less than completely satisfactory for installing surgical wires in the spinal column. Specifically, the sectional dimension of the tubular end portion 40 which is required in order to slidably accommodate the wire 44 in the interior thereof is really almost too large to be accommodated in the foramen 34 of a vertebra without damaging the spinal cord 35. Further, the radius of curvature of the end portion 40 which is required in order to slidably accommodate the wire 44 without significant binding of the wire 44 therein is also relatively large. In addition, the handle 38 and the portions of the wire 44 which extend along the handle 38 tend to make it somewhat clumsy and difficult to delicately manipulate the curved end portion 40 with sufficient precision to assure that the spinal cord 35 is not damaged by the end 42 or other portions of the curved end portion 40 as it is inserted into and withdrawn from the foramen 34 of a vertebra. Also, it is possible to cause damage to the spinal cord 35 when the wire 44 and the instrument 36 are manipulated to pull portions of the wire 44 through the tubular end portion 40. Hence, for all of these reasons, the heretofore-known methods and apparatus for installing surgical wires in the spinal columns of patients have been relatively high-risk procedures which have been less than entirely satisfactory.

Referring now to FIGS. 6 through 8, the method of the instant invention is illustrated. While it will be understood that the use of the method of the instant invention for interconnecting various types of bone structures is contemplated, the method is particularly adapted for use in interconnecting adjacent vertebrae of the spinal column, particularly in the cervical area of the spinal column, such as the vertebrae 20, 22, 24, 26, and 28 hereinabove described in connection with the method of the prior art. The method of the instant invention for installing the surgical wire 10 is preferably carried out by first attaching the wire 10 to a curved surgical needle of the type illustrated in FIGS. 6 and 7 and generally indicated at 46. The needle 46 preferably has a sectional dimension which is approximately equal to the sectional dimension of the main portion 12 of the wire 10, and it preferably has a pointed end 47 and an eyelet 48 at the opposite extremity thereof. The wire 10 is attached to the needle 46 by passing a portion of the leader portion 16 through the eyelet 48 so that the end portion of the leader portion extends back upon itself. Thereafter, the wire 10 is passed through the foramen 34 of a vertebra, such as the vertebra 22, by grasping the needle 46 with a plier-like instrument 49 and passing the needle 46 through the foramen 34 of the vertebra 22 so that the needle 46 passes in closely adjacent relation to the wall of the foramen 34 of the vertebra 22 proximal the lamina 30 thereof. After the needle 46 has been passed through the foramen 34 a sufficient amount so that the end 47 is exposed, the end 47 is grasped with the plier 49 and the leader portion 16 is further advanced to pull the remainder of the leader portion 16, the tapered portion 14 and a portion of the main portion 12 through the foramen 34 as illustrated in FIGS. 7 and 8. Preferably, throughout this procedure a certain amount of tension is applied to the portions of the wire 10 on the opposite sides of the lamina 30 in order to maintain it in engagement with or at least in closely adjacent relation to the wall of the foramen 34, i.e., the undersurface of the lamina 30, so that it does not press against the spinal cord 35. After the wire 10 has been passed through the foramen 34 to the desired extent, it is secured to the adjacent vertebra 24 in order to interconnect the two vertebrae 22 and 24. Preferably this is carried out by passing the wire 10 around the spinous process of the vertebra 24 and then once again passing it through the foramen 34 of the vertebra 22 in a manner similar to that hereinabove described but in the opposite direction and on the opposite side of the spinous process 32 thereof. The two end portions of the wire 10 are then extended along the opposite sides of the spinous process 32 of the vertebrae 22 and along the opposite sides of the spinous process 32 of the vertebra 24, and they are interconnected adjacent the vertebra 24 to provide a wire interconnection which is similar to the interconnection provided by the wire 45 between the vertebrae 24 and 26. Alternatively, the same result can be achieved by separately manipulating the two leader portions 16 at the opposite ends of the wire 10 to install the wire 10 so that it interconnects the vertebrae 22 and 24.

It will be seen that the method of the instant invention has substantial advantages over the heretofore-known methods for interconnecting adjacent bone structures, such as adjacent cervical vertebrae in the spinal column. By utilizing the wire 10 of the instant invention which has a substantially reduced leader portion 16, a needle 46 can be utilized for inserting the wire 10 through the foramen 34 of a vertebra. Accordingly, the sectional dimension of the hardware which is passed through the foramen 34 is minimized, and the curvature of the needle 46 can be selected to precisely meet the needs of each particular application. In addition, since the needle 46 is attached to the leader portion 16 which is highly flexible as a result of its reduced sectional dimension, a substantially greater degree of freedom of movement is available when passing the needle 46 through the foramen 34 so that the needle 46 can be precisely manipulated in the foramen 34 to avoid damage to the spinal cord 35. Further, the wire 10 can be maintained in contact with the wall of the foramen 34 adjacent to the lamina 30 virtually throughout this entire process so that the wire 10 does not press against the spinal cord 35. As a result of these advantages, the method of the instant invention can be effectively practiced with substantially reduced risks to a patient. Specifically, the chances of damaging the spinal cord 35 are substantially reduced when a wire 10 is installed in accordance with the method of the instant invention, and as a result, the chances of causing paralysis to the patient are also substantially reduced. Accordingly, it is seen that the instant invention provides an effective surgical wire and method of installing the wire for interconnecting adjacent vertebrae, and that both the wire and the method for installing the wire have substantial advantages over the heretofore-known apparatus and methods for interconnecting adjacent vertebrae. Hence, for these reasons, it is seen that the wire and method of the instant invention represent significant advancements in the medical art which have substantial merit from the standpoint of minimizing patient risk.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A surgical wire for interconnecting two or more adjacent portions of bone structures and the like in surgical procedures in order to provide support for one of said bone structure portions comprising an elongated substantially smooth flexible and malleable main portion of substantially circular cross section, a substantially smooth flexible and malleable tapered portion of substantially circular cross section which extends integrally from an end of said main portion, and a substantially smooth flexible and malleable leader portion of substantially circular cross section which has a substantially reduced diameter with respect to said main portion and extends integrally from the reduced end of said tapered portion.

2. The surgical wire of claim 1 further comprising a tapered portion and a leader portion at both ends of said main portion.

* * * * *